United States Patent [19]

Cornes

[11] 3,979,667

[45] Sept. 7, 1976

[54] ELECTRICAL INDICATORS

[75] Inventor: Nigel W. Cornes, Hatfield, England

[73] Assignee: Diplex Limited, England

[22] Filed: Dec. 13, 1974

[21] Appl. No.: 532,672

[30] Foreign Application Priority Data

Jan. 2, 1974 United Kingdom................... 156/74

[52] U.S. Cl............................. 324/65 R; 324/65 P; 324/96
[51] Int. Cl.².......................................... G01R 27/20
[58] Field of Search............ 324/65 R, 65 P, 65 CR, 324/65 CP, 158 P; 73/73

[56] References Cited
UNITED STATES PATENTS

| | | | |
|---|---|---|---|
| 3,452,347 | 6/1969 | Stimson | 324/133 |
| 3,688,309 | 8/1972 | Volberg | 324/65 R |
| 3,882,383 | 5/1975 | Matlin | 324/65 P |

*Primary Examiner*—John K. Corbin
*Assistant Examiner*—Wm. H. Punter
*Attorney, Agent, or Firm*—Stevens, Davis, Miller & Mosher

[57] ABSTRACT

A domestic soil-moisture indicator of the kind including a probe comprising a pair of electrodes with spaced ends for insertion in the soil whereby the resistance of the conductive path established between them by the soil to be tested varies in resistance with the moisture of the soil. The improvement comprises a control circuit responsive to the value of the variable resistance and including a pair of light-emitting devices, connected in such a way that the total power between them is substantially constant and, at one end of the scale of value of the variable resistance, one device is fully on and the other is off, while at the other end of the scale the one device is off and the other is fully on, the brightness of the two devices varying between these extremes for intermediate values. The light-emitting devices are preferably light-emitting diodes each of which is connected in series with one of a complementary pair of emitter-following transistors connected to the division point of a potential divider consisting of the variable soil resistance and a fixed resistance connected in series with one another across the source of supply.

2 Claims, 1 Drawing Figure

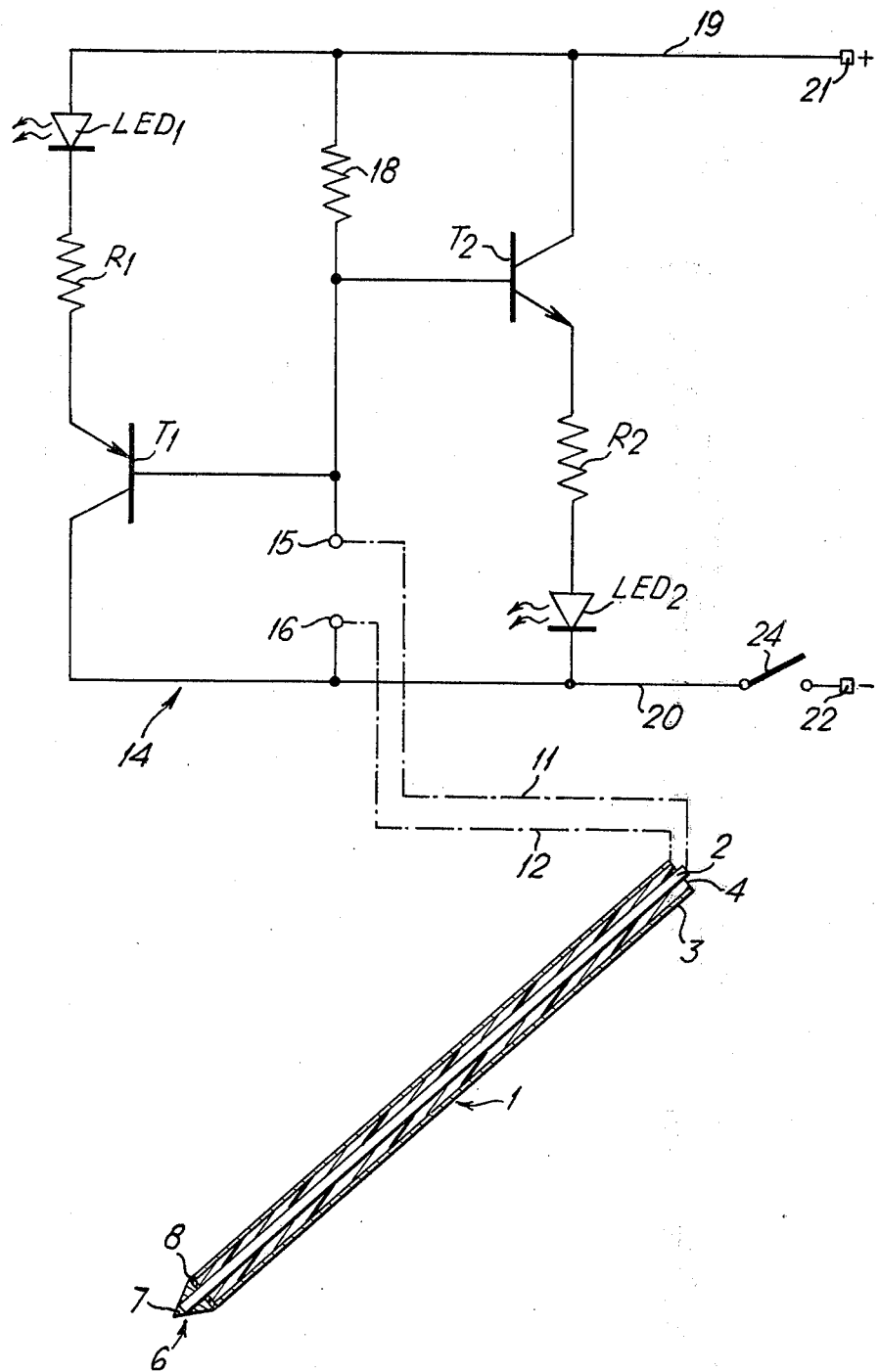

ELECTRICAL INDICATORS

This invention relates to electrical measuring devices, particularly soil moisture indicators, but also including electrical thermometers and other similar devices. Such devices normally respond to a voltage which is a function of the parameter to be measured and in the past this voltage has been measured, for instance by means of a Wheatstone bridge circuit and the value of the parameter has then been displayed, usually by means of a calibrated galvanometer in the circuit.

While such an arrangement is both accurate and reliable, it is not very suitable for the household market, as the equipment, particularly the calibrated galvanometer, tends to be expensive and, in addition, many people do not understand the significance of a parameter expressed on a calibrated scale as, for instance, a percentage.

According to the present invention an electrical measuring device for indicating the value of a single parameter includes a control circuit responsive to the value of the parameter and a number of light-emitting devices controlled by the circuit in such a way that their relative intensities are representative of the value of the parameter. Since it is the relative values of the intensities rather than the absolute values which provide the required indication, the eye is able to arrive at a much closer approximation than if only a single light-emitting device were to be used, for example. In theory it would be possible to replace the calibrated galvanometer referred to above by a light-emitting device, but although this would be considerably cheaper, it would be extremely difficult to judge the intensity of a single light without reference to a standard. By the use of a number of lights of differing intensities, a simple indication is provided and can be understood even by a non-technical user.

Preferably, the device includes just two light-emitting devices connected in such a way that the total power emitted by them is substantially constant and, at one end of the scale of values of the parameter, one device is fully on and the other is off while at the other end of the scale the one is off and the other is fully on, the brightness of the two devices varying between these extremes for intermediate values. In an even simpler arrangement, only one of two light-emitting devices varies in intensity, the other being constant, but this does not give as many different states as if both devices vary. It is also possible to use more than two light-emitting devices.

In order to provide the necessary control of the light-emitting devices, the control circuit may include a resistance which varies with the value of the parameter to be indicated and which is connected in series with a further resistance to constitute a voltage divider across a supply potential, the potential at the division point being connected to control the relative intensities of the light-emitting devices. When such a circuit is used to control a pair of light-emitting devices, each of these may be connected in series with one of a complementary pair of emitter-following transistors across the supply, so that as the potential at the division point varies, the current flowing through the two light-emitting devices varies correspondingly. As a consequence, the value of the parameter can be judged from the relative brightness of the two devices, which constitute reference standards for one another.

When the parameter to be measured is at a maximum a first light-emitting device is fully on and a second light-emitting device is switched off. When the parameter is at a minimum the first light-emitting device is off and the second light-emitting device is fully on. Under any condition between the two extremes both light-emitting devices will be switched on, the relative intensity varying according to the precise value of the parameter. Thus five distinct states will be recognisable, the two states mentioned above, plus three further states in which both light-emitting devices are switched on but in which one or the other is brighter or the two are the same brightness thus indicating above average, below average, and average values of the parameter respectively.

If a control circuit of the kind referred to above is to be used in conjunction with more than two light-emitting devices, each device may be connected in series with a corresponding emitter-following transistor, the successive transistors being connected in cascade. When the parameter to be measured has zero value, all the light-emitting devices are switched off. As the parameter increases in value, a first light-emitting device increases in brightness correspondingly and then the second device switches on, becomes brighter and is successively followed by the remainder of the devices. Thus the number of light-emitting devices that are switched on at any time gives an indication of the value of the parameter. The light-emitting devices themselves are preferably light-emitting diodes, but other forms of optoelectric device may be used instead, e.g. incandescent bulbs.

One application for which a device in accordance with the invention is particularly suitable is for a domestic soil moisture content indicator. Such devices are quite well known in themselves and include a probe comprising a pair of electrodes with spaced ends for insertion in the soil. The soil itself thus defines an electrical path between ends of the two electrodes and the resistance of this path depends on the moisture content of the soil. Leads from the electrodes then need to be connected into the control circuit in such a way that the earth resistance just referred to constitutes the variable resistance of the circuit which is connected in series with a constant resistance to define the voltage divider.

A preferred arrangement of soil-moisture indicator in accordance with the invention will now be described in more detail with reference to the accompanying drawing, which is a circuit diagram.

The probe for insertion in the soil is indicated generally as 1 and includes a central, rod-like electrode 2 and an outer, tubular electrode 3 separated from the electrode 2 by insulating material 4. The probe is formed at one end with a point 6 to assist in inserting it in the soil and, as a result, the end 7 of the electrode 2 is spaced a short distance beyond the corresponding end 8 of the outer electrode 3, the two being separated by an insulating spacer 9. Until the probe is inserted in the soil, there is an open circuit between the ends 7 and 8, but when the probe is inserted in the soil, an electrically conducting path is established whose resistance varies with the moisture content of the soil. When the soil is very dry, the resistance is high and when the soil is very damp, the resistance is low. Accordingly, measurement of the resistance between the two electrodes 2 and 3 provides an indication of the moisture content of the soil.

For measurement purposes, flexible leads 11 and 12 are connected to the rear ends of the electrodes 2 and 3 respectively. A probe of this general type is quite well known and, as mentioned originally, this resistance has previously been measured, e.g. by means of a Wheatstone bridge, so that the resistance, and hence the soil moisture content, could be displayed on a calibrated scale. According to the present invention, however, the resistance is connected in a control circuit indicated generally as 14 which enables the value of the resistance and hence of the soil moisture content to be indicated as a visual display. The leads 11 and 12 are connected to terminals 15 and 16 respectively so that the soil resistance is connected in series with a fixed resistor 18 between supply conductors 19 and 20 connected to terminals 21 and 22 of a direct current supply. The division point of the voltage divider constituted by the resistor 18 and the soil resistance is connected to the base connections of a complementary pair of emitter-following transistors T1 and T2 respectively, each connected in series with a current-limiting resistor R1 and R2 respectively and a light-emitting diode LED1 and LED2 respectively between the supply lines 19 and 20.

When the soil is very dry, so that the resistance between the points 15 and 16 is also very high, the base connections of the two transistors will effectively be at the positive potential of the line 19 so that the transistor T2 carries full current and the other transistor T1 is effectively switched off, thus causing the respective light-emitting diodes LED2 and LED1 to be at full brightness and to be switched off respectively. When the soil is very wet and the resistance between the points 15 and 16 is low, the conditions are reversed, the light-emitting diode LED2 being switched off and the light-emitting diode LED1 being at full brightness. For intermediate conditions when the resistance between the points 15 and 16 is comparable to that of the resistor 18, the two light-emitting diodes will be of equal brightness and, in addition, two other states are readily detectable, i.e. when one light-emitting diode is very much brighter than the other and vice versa, thus giving the five distinct states referred to originally.

In a particular example of the circuit just described, the supply voltage is 9 volts and may conveniently be provided by a battery mounted in the device. The resistor 18 has a value of 10 K, while the two resistors R1 and R2 each have a value of 180r. The two transistors T1 and T2 are respectively types 2N4062 and 2N3711 supplied by Texas Instruments, while the light-emitting diodes are both of the type Hewlett Packard 5082 – 4850. All these components may conveniently be fitted within an enlarged handle fitted to the probe 1 (not shown in the drawing) and the light-emitting diodes may be mounted side by side, for example in the end of the handle where they are readily visible. A switch 24 for controlling the supply is also mounted on the outside of the handle for ready access by the user.

The circuit illustrated may readily be modified for the use of more than two light-emitting devices by the connection of an appropriate number of emitter-following transistors in cascade so that the light-emitting devices are illuminated in succession as described above.

I claim:

1. In a domestic soil-moisture indicator including a probe comprising a pair of insulated electrodes, said electrodes having spaced ends for insertion in soil whose moisture content is to be measured, whereby said soil constitutes a variable resistance between said electrodes, the improvement which comprises a control circuit including a source of electric power, a fixed resistor connected in series with said variable resistance to constitute a voltage divider across said source of supply, said voltage divider having a division point, a pair of light-emitting devices, a complementary pair of emitter-following transistors, said transistors each being connected in series with a respective light-emitting device in opposite senses across said source of supply and connections to said transistors from said division point of said voltage divider, whereby the total illumination emitted by said light-emitting devices is controlled to be substantially constant and, at one end of the scale of values of said variable resistance, one of said devices is fully on and the other said device is off, while at the other end of the scale said one device is off and said other device is fully on, the brightness of said two devices varying between these extremes for intermediate values.

2. An electrical measuring device for indicating the value of a single parameter including a first resistance, said first resistance varying with the value of said parameter to provide a signal dependent on said value, a second resistance connected in series with said first resistance to constitute a voltage divider having a division point, a source of power connected to said resistances, said voltage divider being connected across said source, a plurality of light-emitting diodes and means for controlling the supply of power from said source to said diodes connected to said division point of said voltage divider, said means including a complementary pair of emitter-following transistors, said transistors each being connected in series with a respective light-emitting diode in opposite senses across said source, whereby the current in each said transistor is controlled in accordance with the potential of said division point of said voltage divider so that the total illumination emitted by said diodes is substantially constant and, at one end of the scales of values of said parameter, one of said diodes is fully on and the other diode is off, while at the other end of the scale said one diode is off and the other diode is fully on, the brightness of said two diodes varying between these extremes for intermediate values.

* * * * *